United States Patent [19]

Inbasekaran et al.

[11] Patent Number: 5,288,816
[45] Date of Patent: Feb. 22, 1994

[54] NONLINEAR OPTICAL AMINOARYL HYDRAZONES AND NONLINEAR OPTICAL POLYMERS THEREOF

[75] Inventors: Muthiah N. Inbasekaran; Mark D. Newsham; Michael N. Mang, all of Midland, Mich.

[73] Assignee: The Dow Chemical Company, Midland, Mich.

[21] Appl. No.: 927,692

[22] Filed: Aug. 10, 1992

[51] Int. Cl.$^5$ .................. C08G 59/00; C08G 65/08; C08G 65/14
[52] U.S. Cl. .................. 525/502; 525/504; 528/96; 528/97; 528/98; 528/99; 528/103; 528/107; 528/109; 528/114; 528/116; 528/117; 528/120; 528/123; 528/124; 528/327; 528/407; 428/1; 427/488; 427/491
[58] Field of Search .................. 528/98, 99, 96, 97, 528/103, 107, 109, 117, 116, 120, 123, 124, 327, 407, 422, 114; 525/502, 504

[56] References Cited

U.S. PATENT DOCUMENTS

| | | | |
|---|---|---|---|
| 4,247,477 | 1/1981 | Gruber et al. | 564/251 |
| 4,468,494 | 8/1984 | Barton et al. | 525/353 |
| 4,621,156 | 11/1986 | Barton et al. | 564/250 |
| 4,732,904 | 3/1988 | Morgan | 514/357 |
| 4,867,540 | 9/1989 | Demartino | 350/355 |
| 4,909,608 | 3/1990 | Frazier, III | 350/354 |
| 5,208,299 | 5/1993 | Bales et al. | 528/125 |

FOREIGN PATENT DOCUMENTS 0099552 7/1983 European Pat. Off. .
363237A3 11/1990 European Pat. Off. .
62-210431 3/1986 Japan .

Primary Examiner—Frederick Krass

[57] ABSTRACT

The present invention relates to nonlinear optical materials comprising aminoaryl hydrazones and to nonlinear optical polymeric compositions containing recurring covalently bonded moieties derived from the aminoaryl hydrazones of the invention. The polymeric compositions of the present invention have high glass transition temperatures and exhibit stable nonlinear optical activity at high temperatures over a period of time.

36 Claims, No Drawings

NONLINEAR OPTICAL AMINOARYL HYDRAZONES AND NONLINEAR OPTICAL POLYMERS THEREOF

FIELD OF THE INVENTION

The present invention relates to aminoaryl hydrazones exhibiting nonlinear optical properties, and to materials comprising moieties derived from nonlinear optical aminoaryl hydrazones. More particularly, the present invention relates to novel nonlinear optical (NLO) polymeric compositions obtained by reacting epoxy containing compounds with the nonlinear optical aminoaryl hydrazones of the invention.

BACKGROUND OF THE INVENTION

Nonlinear optical (NLO) materials have been used in electro-optic devices for more efficient processing and transmitting of information in the field of fiber optic communications. The NLO materials used in these devices have in general been inorganic crystals such as lithium niobate ($LiNbO_3$) or potassium dihydrogen phosphate (KDP). More recently, nonlinear optical materials based on organic molecules, and in particular polar aromatic organic molecules, have been developed.

Organic nonlinear optical materials have a number of potential advantages over inorganic materials. Specifically, they have fast response times, small dielectric constants, good linear optical properties, large nonlinear optical susceptibilities, and high damage thresholds. In addition, organic materials can be easily fabricated into integrated device structures when used in polymer form. Organic crystals of 2-methyl-4-nitroaniline have been shown to have a higher nonlinear optical activity than that of $LiNbO_3$.

There are various known polymeric organic materials which possess specific nonlinear optical properties and various known processes for making such polymeric organic materials. Many of the current polymeric organic materials prepared by the prior art are prepared by blending a NLO molecule into a polymer host material. "Blending" herein means a combination or mixture of materials without significant reaction between specific components.

EP 218,938 and U.S. Pat. No. 4,859,876 have used an approach of incorporating NLO active molecules into amorphous polymer host matrices for NLO media. EP 218,938 discloses a number of polymer host materials, including epoxies, and many types of molecules which have NLO activity including azo dyes such as Disperse Red 1. It is known that an NLO active material such as azo dye Disperse Red 1, (4, -[N-ethyl-N-(2-hydroxyethyl]amino-4-nitro azobenzene), may be incorporated into a host by simply blending the azo dye in a thermoplastic material such as poly(methylmethacrylate), as described in Applied Physics Letters 49(5), 4 (1986) and U.S. Pat. No. 4,859,876.

While the doped polymer approach offers some advantages over organic and inorganic crystals, the approach has a number of problems. First, the stability of the NLO activity over time for such materials has been shown to be poor. A problem associated with a polymer with NLO properties produced by simply blending NLO molecules into a host polymer is that these polymer materials lack orientational stability. There is significant molecular relaxation or reorientation within a short period of time resulting in a loss of NLO properties. For example, as reported by Hampsch et al., Macromolecules 1988, 21, 528-350, the NLO activity of a polymer with NLO molecules blended therein decreases dramatically over a period of days at room temperature.

In addition, the NLO dopants in the blended polymeric media plasticize the polymer host matrix, lowering the polymer glass transition temperature (Tg). Lowering the polymer $T_g$ has the effect of lowering the temperature stability of the electrically oriented NLO material or NLO medium. Near the Tg, segments of the polymer become mobile and the NLO active dopant molecules which are oriented electrically undergo orientational relaxation. Once orientational relaxation has occurred, the NLO medium exhibits no NLO activity.

A third problem with the doped polymers is the poor solubility of the NLO chromophore in the host matrix. This limits the concentration of NLO properties that can be incorporated in the polymer matrix. Finally, the NLO chromophores tend to aggregate at relatively low doping levels (e.g. 5-20 percent w/v). Such aggregates scatter light and reduce the transparency of the waveguides to unacceptable levels.

Another disadvantage is that the polymer employed may have a low glass transition temperature, or lack sufficient tensile strength or other desirable properties for optical devices.

Generally, the incorporation of molecular structures which have NLO activity into the backbone of a polymer chain will decrease the likelihood of the structural reorganization in comparison with polymers in which the NLO active molecule is simply blended. It is, therefore, desirable to provide a polymer material with NLO groups covalently bonded to the backbone of the polymer material to minimize relaxation effects.

Amine curing agents have long been used as curing agents for epoxy resins. Amine curing agents are discussed in Lee and Neville, *Handbook of Epoxy Resins*, McGraw Hill (1967), pages 8-1 to 8-18 and 9-1 to 9-15. Amine curing agents are also discussed in U.S. Pat. Nos. 4,330,659 4,814,414, and 4,822,832.

Japanese laid open publication Nos. J-63-275,553 and J-62-210,431 disclose various organic nonlinear optical compounds containing hydrazone functionalities which are useful for NLO applications. Specifically, J-62-210,431 discloses nonlinear optical materials containing nonlinear optical hydrazones as powders, molecule inclusions within the host lattice, thin layers deposited upon carriers such as films, monocrystals, and solutions. The hydrazones of J-62-210,431 may be bonded in the form of a pendant group to a polymer such as a polydiacetylene.

It is an object of the present invention to provide nonlinear optical aminoaryl hydrazones as curing agents for epoxy resins, and as suitable monomers for polymeric compositions such as poly(amino ethers), polyimides, polyamides, and polyureas.

It is further the object of the present invention to provide epoxy polymers or epoxy based polymers containing covalently bonded aminoaryl hydrazone moieties in the structure of the polymers exhibiting enhanced nonlinear optical activity and stability.

It is an additional object of the present invention that the polymers comprising the NLO materials have relatively high glass transition temperatures. A high glass transition temperature will correlate with high temperature stability of the NLO material or medium.

SUMMARY OF THE INVENTION

According to the present invention, there is provided a nonlinear optical material comprising aminoaryl hydrazone moieties exhibiting nonlinear optical properties, represented by the formula:

wherein Ar is a substituted aromatic carbocyclic or heterocyclic radical containing up to 30 non-hydrogen atoms, optionally substituted with a functionality capable of reacting with an epoxy group; A is independently at each occurrence either R or substituted aromatic group, optionally substituted with a functionality capable of reacting with an epoxy group; D is selected from a group consisting of covalent bond, carbonyl or sulfonyl containing group; and R is hydrogen or a $C_1$ to $C_{20}$ hydrocarbyl radical; provided there is at least one aromatically substituted electron withdrawing group, and at least two active aromatic amino hydrogens capable of reacting with an epoxy group, in the aminoaryl hydrazone molecule.

In another embodiment, the invention is a nonlinear polymeric composition comprising the reaction product of:

(A) at least one compound selected from a group consisting of a compound containing an average of more than one epoxy group per molecule; and (B) comprising at least a first reactant represented by the formula:

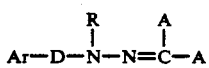

wherein Ar is a substituted aromatic carbocyclic or heterocyclic radical containing up to 30 non-hydrogen atoms, optionally substituted with a functionality capable of reacting with an epoxy group; A is independently at each occurrence either R or a substituted aromatic group, optionally substituted with a functionality capable of reacting with an epoxy group; D is selected from the group consisting of covalent bond, carbonyl or sulfonyl containing group; and R is hydrogen or a $C_1$ to $C_{20}$ hydrocarbyl radical; provided there is at least one aromatically substituted electron withdrawing group, and at least two active aromatic amino hydrogens capable of reacting with an epoxy group, in the aminoaryl hydrazone molecule.

In still another embodiment, the invention is a process of preparing a nonlinear optical polymeric composition of the invention comprising applying an electric field to the polymeric composition described above.

DETAILED DESCRIPTION OF THE INVENTION

Suitably, Ar is selected from a group consisting of:

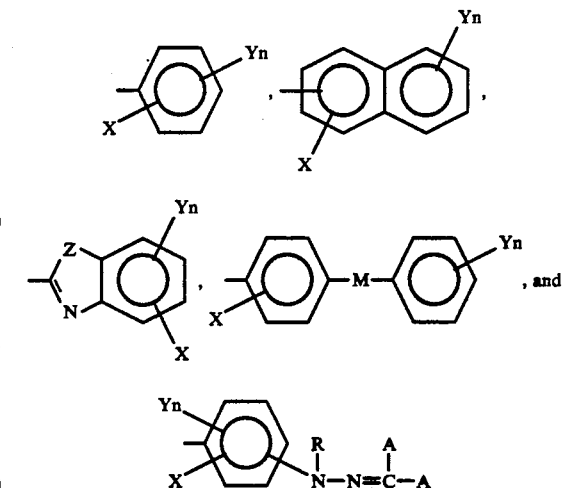

wherein X is a hydrogen or a functionality capable of reacting with an epoxy group: Z is selected from a group consisting of O, S and NR; M is either a covalent bond or a divalent conjugated group; Y is a hydrogen or an electron withdrawing group; n is an integer from 1 to 5; and R is as defined hereinabove, provided that when X is a hydrogen, Y is not a hydrogen.

The term "electron withdrawing", as employed herein, refers to any substituent which attracts the electrons from a conjugated electron structure, thereby providing a polarized resonating structure. A quantification of the level of electron-withdrawing capability is given by the Hammett $\sigma$ (sigma) constant. This well known constant is described in many references, for instance, J. March *Advanced Organic Chemistry* (McGraw Hill Book Company, New York, 1977 edition) p. 251-259. The Hammett constant values are negative for electron donating groups ($\sigma_p$ —0.66 for $NH_2$) and positive for electron withdrawing groups ($\sigma_p$=0.78 for a nitro group, $\sigma_p$ indicating para substitution.)

Preferred electron withdrawing groups are those having a Hammett constant of ($\sigma_p$) at least 0.50, and more preferably at least 0.60.

Illustrative of the electron withdrawing groups useful in the present invention include: $-NO_2$, $-SO_2R$, $-SO_2CH_2F$, $-SO_2CHF_2$, $-SO_2CF_3$, $-S(-NSO_2CF_3)CF_3$, $-CF_3$, $-CO_2R$, $-COCF_3$, cyano, cyanovinyl, dicyanovinyl, and tricyanovinyl, wherein R is as previously defined.

The term "conjugated" group, as employed herein refers to a moiety containing alternating double or triple bonds which has the ability to transfer electronic charge. Conjugated moieties generally include groups which have, for example, a hydrocarbyl diradical comprising a single aromatic ring, multiple fused rings or multiple aromatic rings linked by carbon-carbon, carbon-nitrogen, or nitrogen-nitrogen double bonds. The conjugated groups may be substituted with pendant radicals such as alkyl, aryl, cyano, halo and nitro groups.

Functionalities capable of reacting with the epoxy groups are discussed in Lee and Neville, *Handbook of Epoxy Resins*, McGraw Hill (1967), pages 5-1 to 5-40. Illustrative of the functionalities capable of reacting with the epoxy group represented by X include: $-OH$, $-NH_2$, $-NHR$, $-CO_2H$, $-SH$, $-CHO$, $-COCl$, —Cl, —OOH, —COOCOR, and —CONHR, wherein R is as described previously.

Illustrative divalent conjugated groups, represented by M in the instant invention, include: —C≡C—, —CR=CR—, —CR=CR—CR=CR—, —CR=N—, —N=CR—, and —N=N—, wherein R is as defined hereinbefore.

The term "aromatically substituted" refers to groups that are directly attached to an aromatic ring.

Preferably, substituent A independently at each occurrence is selected from:

wherein X, and Y, are as defined previously, and m+n is equal to 5, provided that when X is a hydrogen, Y is not a hydrogen.

Arylhydrazones of the present invention are preferably aminoaryl hydrazones. The aminoaryl hydrazone preferably contains at least one primary aromatic amino group as a first functionality capable of reacting with an epoxy group. Preferred aminoaryl hydrazones, for example, include derivatives of substituted aminobenzophenones and acetoaminophenone. More preferred hydrazones of the invention further contain a second functionality capable of reacting with an epoxy group. The second functionality is preferably a hydroxyl or an aromatic amino group capable of reacting with the epoxy group. More preferred aminoaryl hydrazones, for example, include those derived from hydroxyaminobenzophenone. Most preferred hydrazones of the invention are those wherein the second functionality is a primary aromatic amino group. Illustrative of the most preferred hydrazones are those derived from diaminobenzophenones.

Amino arylhydrazones of the present invention can suitably be prepared, in general, by the reaction of a suitable hydrazine with a compound having one or more carbonyl group, especially aldehydes or ketones.

Suitable hydrazines include those having the formula:

where R and Ar are as defined hereinabove.

Illustrative but not limiting of the hydrazines include 4-nitrophenylhydrazine, 2,4-dinitrophenylhydrazine, 3-hydroxy-4-nitrophenylhydrazine, N'-methyl-N'-(3-hydroxy-4-nitrophenyl) hydrazine, N'-methyl-N'-4-(nitrophenylhydrazine), 6-nitro-2-benzothioazolylhydrazine, N'-methyl-N'[4-(p-hydroxyphenylsulfonyl)phenyl]hydrazine, 2,4-dinitro-1,5-bis-hydrazino benzene, 2,4-bis(methylsulfonyl)phenylhydrazine, 4-(methylsulfonyl)phenylhydrazine. Preferred hydrazines useful for the present invention are substituted nitrophenylhydrazines.

Suitable carbonyl containing compounds for the purpose of this invention are of the general formula:

where A is independently at each occurrence as previously defined.

Illustrative but not limiting of the carbonyl containing compounds include 4,4'-diaminobenzophenone, 3,3'-diaminobenzophenone, 3,4-diaminobenzophenone, m-aminoacetophenone, 3-hydroxy-4-nitrobenzaldehyde, and p-aminoacetophenone.

Nonlinear optical materials comprising dihydroxyaryl hydrazones, and nonlinear optical polymeric compositions comprising recurring divalent moieties of dihydroxyaryl hydrazones have been described in U.S. patent application Ser. No. 866400 now U.S. Pat. No. 5,208,299.

The hydrazones of the present invention can be provided by a suitably catalyzed reaction of a desired hydrazine compound with desired carbonyl containing reactants as are set forth hereinbefore. A catalyst such as a mineral acid or other acid is generally employed to increase the rate of the reaction. Acetic acid or sulfuric acid are suitably used as catalysts and permit the convenient production of the desired hydrazone compound. Preferably, the hydrazine compound is employed in an amount substantially equivalent with the available carbonyl content of the aldehyde or ketone. The reactants can be employed in a suitable solvent such as ethanol, methanol, m-xylene and such and brought to boiling. A catalyst such as acetic acid is added and additional solvent, where needed, can be added to obtain a solution of reactants. Upon cooling, the hydrazone is precipitated and recovered, as by filtration. The hydrazone recovered upon cooling can be recrystallized from a suitable solvent such as ethanol, ethanol-water mixture and the like.

The aminoaryl hydrazones containing tricyanovinyl group are best prepared by reacting 1-formyl-2-tricyanovinylphenylhydrazine with a carbonyl compound in aqueous ethanol containing a mineral acid as taught by J. R. Roland and B. C. McKusick [(J. Amer. Chem. Soc. 83, 1652 (1961)]. 1-formyl-2-tricyanovinylphenylhydrazine is synthesized by reacting 1-formyl-2-phenylhydrazine with tetracyanoethylene as reported in the above reference.

The aminoaryl hydrazones of the invention exhibit nonlinear optical properties when subjected to an electric field. Electric Field Induced Second-Harmonic Generation (EFISH(G)) has been used to determine the hyperpolarizability ($\beta$) via the $\mu\beta$ product, where $\mu$ is the dipole moment of the hydrazone molecule. The methodology used is described by B. F. Levine and C. G. Bethea, J. Chem. Phys. 63, 2666–2682 (1975), incorporated herein by reference.

The aminoaryl hydrazone of the present invention is suitable as a curing agent for epoxy resins, or as a monomer for polymeric compositions which, for example, include poly(amino ethers), polyimides, polyamides, and polyureas. The aminoaryl hydrazone is incorporated as recurring covalently bonded moieties into the structure of the polymer, which exhibits nonlinear active properties when oriented by the application of an external field such as an electric field, magnetic field, or mechanical force. The aminoaryl hydrazone provides the NLO chromophore in the resulting polymeric composition.

The incorporation of the NLO active structures into the polymer structure has a number of advantages. High levels of NLO chromophore functionalization can be achieved without increasing the scattering losses of waveguides fabricated from the polymer. The addition of the groups which add to the NLO activity of the polymer do not plasticize the polymer and lower the polymer $T_g$. In fact, such modifications can raise the polymer $T_g$. Furthermore, the fact that the NLO chromophore is inherent to the polymer backbone increases the orientational stability of the NLO chromophores, reducing the temporal decay of the NLO activity with time. Thus, polymers containing this monomer have the advantage of high $T_g$ and increased orientation stability when fabricated into a nonlinear optical film or other NLO article in comparison to other NLO polymers.

The present invention provides polymeric compositions which are thermoplastic and thermoset compositions with good thermal stability. Thermoplastic compositions are represented, for example, by poly(amino ethers), polyimides, polyamides and polyureas.

Poly(amino ethers) are the most suitable thermoplastic compositions for the purposes of this invention. The thermoplastic poly(amino ethers) are obtained by reacting at least a first component (A), an epoxy-containing compound, with component (B) by melt or solution polymerization methods known in the art.

The component (A) for obtaining poly(amino ethers) of the invention is generally any compound having an average of no more than two vicinal epoxide groups per molecule. More preferably, the component (A) may be any compound that contains an average of no more than two glycidyl group per molecule. Even more preferably, the component (A) can be glycidyl ethers, glycidyl esters or glycidyl amines. Most preferably, component (A) is a diglycidyl ether of dihydric phenols. Examples of suitable dihydric phenols include: bisphenol A; 4,4'-dihydroxydiphenylethylmethane; 3,3'-dihydroxydiphenyldiethylmethane; 4,4'-dihydroxydiphenyloxide; 4,4'-dihydroxybiphenyl; 4,4'-dihydroxybenzophenone; 4,4'-dihydroxydiphenylsulfide; and 4,4'-dihydroxydiphenylsulfone. Suitable dihydric phenols are described in U.S. Pat. Nos. 3,395,118; 4,438,254; and 4,480,082 incorporated herein by reference.

Any combination of the aforementioned epoxy-containing compounds may be used herein. Therefore, another embodiment of the present invention is the use of a mixture or a blend of epoxy-containing compounds as component (A).

The component (B) comprises at least a first reactant, the aminoaryl hydrazone of the invention, for reacting with the epoxy-containing component (A). Generally, the aminoaryl hydrazone of the invention for obtaining the thermoplastic poly(amino ethers) contains at least one primary aromatic amino or two secondary aromatic amino groups as the functionalities capable of reacting with the component (A).

Desirably, the aminoaryl hydrazone contains one primary aromatic amino group as a first functionality capable of reacting with the epoxy group. Illustrative but not limiting of the arylhydrazones used for obtaining thermoplastic poly(amino ethers) are nitrophenyl hydrazones of acetoaminophenones.

The component (B) may further contain a second reactant for reacting with the epoxy compound. Examples of second reactants include primary aromatic amines such as aniline, or bis-secondary amines such as piperazine or N,N'-dimethyldianiline. Therefore, still another embodiment of the poly(amino ethers) of the invention is the use of a mixture of the reactants comprising component (B).

Poly(amino ethers) of the present invention are suitably prepared by contacting one or more epoxy-containing component (A) with aminoaryl hydrazone of the invention containing one primary aromatic amino group under conditions sufficient to cause the amine moieties to react with epoxy moieties to form a polymer backbone having amine linkages, ether linkages and pendant hydroxyl moieties. Conditions suitably employed in preparing the resins of this invention are those conventionally employed in the reaction of diglycidyl ethers with amines to form amine linkages and pendant hydroxyl groups. Examples of such suitable conditions are set forth in U.S. Pat. No. 3,317,471, which is hereby incorporated by reference in its entirety. In general, however, the process for preparing the polymers is carried out so that the unreacted epoxy groups in the finished poly(amino ether) are minimized. By minimizing the epoxy groups in the poly(amino ether) the essential thermoplastic character of the poly(amino ether) can be retained. Preferred conditions for preparing such resins are set forth in the working examples provided hereunder.

Preferably the mole ratio of component (A) to that of component (B) is between about 0.97 to about 1.03. Optionally a capping agent may be added to the reaction mixture for minimizing the unreacted terminal epoxy groups in the poly(amino ether). Illustrative but not limiting of suitable capping agents are t-butyl phenol, piperidine, and 2-hydroxyethyl piperazine.

The thermoplastic polymeric compositions are used to fabricate a film by methods described below. The film is subjected to electric field poling as set forth hereinbelow to obtain a non-centrosymmetric alignment of the dipolar segments throughout the bulk of the polymer film. Nonlinear optical activity exhibited by the poled film is attributed to such a non-centrosymmetric alignment of the dipolar segments in the polymer.

The thermoplastic products obtained in the invention may be cross-linked to obtain a thermoset composition by further reaction with the hydroxyl groups of the product as is known in the art for epoxy coatings.

As an illustration, one embodiment of the thermoset compositions of the invention is produced by reacting at least a first component (A) with component (B) comprising at least a first reactant which is the aminoaryl hydrazone of the invention.

The component (A) for obtaining thermoset compositions of the invention includes a wide variety of epoxy-containing compounds. Generally, the first component (A) is any compound having an average of more than one vicinal epoxide group per molecule. More preferably, the component (A) may be any compound containing an average of more than one glycidyl group per molecule. Even more preferably, the component (A) can be glycidyl ethers, glycidyl esters or glycidyl amines.

Illustrative of the preferred glycidyl ethers used in preparation of the thermoset compositions of the present invention are the glycidyl ethers of polyhydric phenols including for example, the glycidyl ethers of phenol or substituted phenol such as the aldehyde novolac resins, particularly phenol-formaldehyde resins and cresol-formaldehyde resins. The glycidyl ethers of polyhydric phenols also may include the glycidyl ethers of bisphenols or substituted bisphenols such as the glycidyl ether of bisphenol A and triglycidyl ether of 4,4',4"-trihydroxyphenyl methane. Other examples of glycidyl ethers of polyhydric phenols useful in the present invention are described in U.S. Pat. No. 4,330,659 incorporated herein by reference, for example diglycidyl ethers of bisphenols corresponding to the formula:

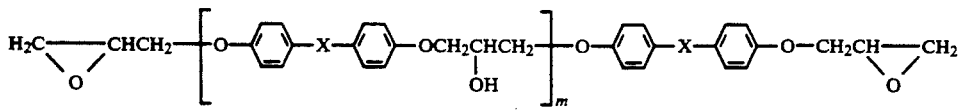

wherein m is from 0 to about 50 and X is —CH$_2$—, —C(CH$_3$)$_2$—, —SO$_2$—, or

These represent, respectively, bisphenols F, A, S and AP. Other applicable ethers include the diglycidyl ethers of resorcinol, catechol, hydroquinone, and the like. The various ethers may be substituted on the respective phenyl rings by such non-reactive substituents as alkyl, halogen, and the like. The glycidyl ethers of compounds having more than one aromatic hydroxyl group per molecule are disclosed in U.S. Pat. No. 4,829,133, incorporated herein by reference for the teachings of these epoxy resins. The glycidyl ethers of hydrocarbon-phenol resins disclosed in U.S. Pat. No. 4,710,429, incorporated herein by reference, may also be used in the present invention.

Component (A) of the present invention also includes di- or polyepoxides of aliphatic or cycloaliphatic compounds containing more than one epoxidizable unsaturated group, for example, the diepoxides of cyclohexadiene, butadiene and the like.

The epoxy-containing compound suitably used herein can be a monomer, oligomer or polymer resin. Epoxy monomers and oligomer units suitably used herein are described in the *Encyclopedia of Chemical Technology*, vol. 9, pp 267-290, published by John Wiley & Sons, 1980. Examples of the epoxy resins suitably used herein include novolac epoxy resins such as cresolnovolac epoxy resins and epoxy phenol novolac resins; bisphenol-A epoxy resins such as diglycidyl ethers of bisphenol A; cycloalkyl epoxy resins; glycidyl amine resins; triazine resins; hydantoin epoxy resins and combinations thereof.

Some commercial epoxy resins useful in the present invention include, for example, D.E.R. TM 331, D.E.R. TM 332, D.E.R. TM 383, D.E.R. TM 431, D.E.R. TM 736, and Tactix TM 742, all commercially available from the Dow Chemical Company.

Any combination of the aforementioned epoxy-containing compounds may be used herein. Therefore, another embodiment of the present invention is the use of a mixture or a blend of epoxy-containing compounds as component (A).

The epoxy containing component (A) used herein may also comprise an epoxy compound which exhibits a NLO response. An example of an epoxy compound exhibiting a NLO response is described in U.S. Pat. No. 5,112,934 incorporated herein by reference.

The component (B) comprises at least a first reactant which is the aminoaryl hydrazone of the invention. Suitably, the arylhydrazone for obtaining the thermoset compositions of the invention contains a primary aromatic amino group as a first functionality capable of reacting with the epoxy group and further contains a second functionality capable of reacting with the epoxy group. Preferably, the second functionality is a hydroxy group. Illustrative but not limiting of preferred arylhydrazones are 3-hydroxy-4-nitrophenylhydrazone of 3-aminoacetophenone, and 4-aminobenzoylhydrazone of 3-hydroxy-4-nitrobenzaldehyde. Most preferably, the second functionality is a primary aromatic amino group. Illustrative but not limiting of the most preferred arylhydrazones are 4-nitrophenylhydrazones of 4,4'-diaminobenzophenone, 3,3'-diaminobenzophenone, and 3,4-diaminobenzophenone; 2,4-dinitrophenylhydrazone of 4,4'-diaminobenzophenone, 3,3'-diaminobenzophenone.

The thermoset polymeric compositions are the more preferred compositions of the invention, for they provide a crosslinked polymeric network responsible for providing compositions with higher glass transition temperatures and enhanced thermal stability of NLO activity. The epoxy based thermoset polymers per se have heretofore been shown to have resistance to chemical attack.

The thermoset polymeric compositions of the present invention are obtained by making a prepolymer by reacting component (A) with component (B) of the invention by melt or solution polymerization methods known in the art. The prepolymer is used to form a film by methods described hereinbelow. The film so obtained is cured to provide the cross-linked thermoset polymeric composition of the present invention.

For the thermoset polymeric compositions, component (B) may further comprise one or more second reactants or curing agents capable of reacting with the epoxy groups such as described in U.S. patent application Ser. No. 800,345, now U.S. Pat. Nos. 5,173,546, 844,340, and 852,924 and incorporated herein by reference.

Preferably, the second reactant or the curing agent is a compound which exhibits a NLO response. Nonlinear optical active amine curing agents, and crosslinked epoxy polymers thereof, exhibiting nonlinear optical activity have been described in the application Ser. No. 800,345, now U.S. Pat. Nos. 5,173,546, 844,340, and 852,924. An example of a second reactant or curing agent which exhibits a NLO response and may suitably be used herein is 4,4'-diaminodiphenyl sulfone as disclosed in U.S. Ser. No. 852,924.

Generally, the amounts of components (A) and (B) employed herein are sufficient to provide a cured product. Usually the amounts of components (A) and (B) which provide a ratio of equivalents of curing agent per epoxy groups of from about 0.5 to about 1.2; preferably from about 0.75 to about 1.1 and more preferably from about 0.95 to about 1.05 are used herein.

The percentage of first reactant should be sufficient to provide the final cured product with NLO properties. Generally the percent of the first reactant used herein may be from about 0.1 percent of about 100 percent with respect to the amount of reactant. It is preferable to use at or near 100 percent of the first reactant. The percentage of the second reactant or curing agent used may be the remainder if anything less than 100 percent of the first curing agent is used.

Various factors will affect the range of the percentage of the first and the second reactants relative to the number of epoxy groups. These factors include the optical absorption of the NLO group, the level of stability required, and the strength of the NLO group. In general, the level of addition of NLO moieties to polymer will be as high as possible to maximize the NLO effect. The level of addition will be balanced by the stability and quality of the film desired to be produced.

It may be desirable to employ a catalyst to accelerate the epoxy/curing agent reaction. Suitable catalysts which can be employed are described in U.S. patent application Ser. Nos. 800,345, 844,340, and 852,924 incorporated herein by reference.

The most preferred catalyst used is 2-methyl imidazole due to the reduction in ionic species in the resulting product material by its use. The reduction of ionic species in the polymer material is important for its reduction of conductivity which can lead to a catastrophic dielectric breakdown during the orientation process of the polymer product.

The reaction conditions used for preparing the prepolymer for the thermoset polymer composition of the present invention will vary depending on the particular reactants used. Preferably, the reactants, i.e. components (A) and (B), are added to a reaction flask and heated under a nitrogen atmosphere to initiate the standard epoxy ring opening reaction. The reaction process of the present invention is preferably carried out at a temperature of from about room temperature (about 20° C.) to about 300° C. and more preferably from about room temperature to about 250° C. Above about 300° C. degradation of the epoxy polymer may occur and below about room temperature no reaction may occur. Optionally, the reactants are degassed to less than about $1 \times 10^{-2}$ Torr. The degassing is preferred to remove bubbles and moisture which may degrade the final properties of the product. The degassing is generally carried out at a temperature at which the reactants have a reduced viscosity. While the degassing temperature depends on the reactants used, generally the degassing temperature is below the temperature of sublimation of reactants or below the reaction temperature. The reaction mixture is heated optionally under nitrogen. Generally, the period of time for the reaction depends on the kinetics of the particular reactants, but preferably the reaction time is less than 5 hours and more preferably less than 1 hour. The reacted mixture is then cooled to room temperature for use. This product is generally soluble in common solvents.

In the instances where neither component (A) nor component (B) melts at a sufficiently low temperature, the prepolymer must be prepared in solution.

Suitable solvents which can be employed herein include, for example, glycol ethers, ketones, aromatic hydrocarbons, alcohols, amides, combinations thereof and the like. Particularly suitable solvents employed herein include, for example, methyl ethyl ketone, acetone, methanol, dimethylformamide, dimethylacetamide, ethylene glycol methyl ether, propylene glycol methyl ether, combinations thereof and the like.

As an illustration of another embodiment of the process of the present invention, a prepolymer is first prepared by reacting component (A) with less than 100 percent of a first reactant of the invention and then reacting the prepolymer with a second curing agent.

The prepolymer may be fully cured using a second curing agent such as 4,4'-diaminodiphenyl sulfone (DADS), which exhibits nonlinear optical properties. The final product so obtained exhibits certain improved properties such as greater stability and higher glass transition temperature. A sufficient amount of the second curing agent is added to the prepolymer to substantially react all of the remaining epoxy groups, and to provide a film with improved quality, optical clarity and stability.

The polymeric composition of the present invention generally exhibits a glass transition temperature of from about 90° C. to about 300° C., preferably above about 140° C. and more preferably above about 160° C.

The polymeric compositions of the present invention can be in the form of sheets, films, fibers or other shaped articles formed by conventional techniques. Generally, films are used in testing, electro-optic devices and waveguide applications.

Methods of fabricating films of NLO polymers and the methods of characterization of NLO activity are well known to those skilled in the art. Polymer films are typically fabricated by spin-coating or dip-coating a polymer solution onto a substrate. The substrate used depends on the poling method and method of characterization. For corona poling, a glass substrate such as a microscope slide is typically used. For parallel plate poling, a substrate with an electrically conductive surface is necessary, such as indium-tin-oxide (ITO) coated glass. The coated glass slides can be used directly for corona poling. The coated ITO slides for parallel plate poling require an electrically conductive overlayer, such as sputter-coated gold.

For thermoset polymeric compositions, the mixture of epoxy resins reacted with a first reactant of the invention possibly with the addition of the second curing agent is placed on a surface to make a film. The film may be produced in a number of ways. For many prepolymer mixtures with low viscosity a substrate is required. The mixture may be spread over the surface by compression with another substrate, or by dip, spray, or spin coating. Thermal processing of the mixture deposited on a substrate and the ultimate thermal and mechanical properties of the resultant polymer are dependent on the type of epoxy resin and curing agent utilized. The degree of stability required will then determine the type of polymer components needed. The techniques for mixing and polymerizing are similar to those known in the art. One aspect of the polymerization which improves the mechanical properties of the film is the schedule of temperature ramping of the mixture to its final cure temperature. By staging the cure at intermediate temperatures the optimal network structure is obtained. Retaining the final cure temperature for a period of hours is often necessary for the most complete polymerization possible. The long term chemical and mechanical stability of the final polymer will be dependent on the network formed.

A film can be prepared, for example, by constraining a mixture of components (A) and (B) between two planar substrates and then polymerizing the mixture to form a thin film. The films used for testing electro-optic devices and waveguides should be thin films. Generally, the film has a thickness of from about 0.5 μm to about 500 μm. Preferably, the thickness of the film is from about 1 μm to about 25 μm.

The fabricated NLO film must have a non-centrosymmetric alignment of the dipolar segments throughout the bulk of the polymer film. The orientation of the dipole segments in the polymer may be achieved by applying an external field such as an electric field, magnetic field, or mechanical force to the polymer film.

In electric field poling, the thermoset or thermoplastic polymeric material is preferably raised above its glass transition temperature, $T_g$, because in this state, large scale molecular motion is enhanced. An intense electric field is then applied to the polymeric composition to align the nonlinear optic moieties. Electric field strengths of between about 0.05 to about 2.0 megavolts per centimeter (MV/cm) can be applied. The film is then cooled to room temperature with the electric field still applied. The field is then removed, resulting in a system where the nonlinear optical moieties are aligned within the polymer matrix.

In corona poling, the field results from a discharge between a wire, such as tungsten, suspended above the film and a grounded heater block. The corona poling technique is described further by M. A. Mortazavi, et al., J. Opt. Soc. Am. B 6, (1989). In parallel plate poling, a voltage is applied across the two electrode layers. In both procedures a voltage is applied at elevated temperatures, near the polymer Tg (approximately 5°-10° C. above the onset of Tg as measured by DSC). The field is left on for at least a few minutes and the sample cooled with the field on to maintain the orientation of the dipolar segments.

Another method of orientation of the thermoset polymer of the present invention for producing nonlinear optical materials includes polymerizing the prepolymer of a thermoset polymeric composition of the invention while the prepolymer is under an electric field such that the nonlinear optical moieties are aligned in the electric field before complete polymerization of the prepolymer takes place. This method of orientation will produce less stress on the ultimate polymer network than if the electric field is applied after the NLO moieties are incorporated into the backbone of the polymer.

Still another method for preparing thin films for nonlinear optical applications includes annealing of the polymer while simultaneously poling the polymer which will allow relaxation of the polymer around the oriented molecule. After the temperature of a polymer has been raised to above the Tg and the polymer has been poled, the temperature is reduced from about 10° C. to about 30° C. below the Tg and maintained at this lower temperature to allow for densification. This "annealing" step is carried out so as to cause a reduced free volume in the film and thus less room for NLO moieties to randomly reorient themselves which can lead to a decrease in the NLO signal. Thus, this annealing process during polymer orientation may advantageously improve the stability of the polymer.

The oriented film fabricated from the polymers of this invention can be characterized for their NLO activity by a Maker Fringe Rotation Second Harmonic Generation Technique which is well known to those skilled in the art. See for example, Singer et al., Appl. Phys. Lett. 49, (1986) 248-250.

The following preferred specific embodiments are to be construed as merely illustrative, and not limitative of the remainder of the disclosure in any way whatsoever. In the following examples, all temperatures are set forth uncorrected in degree Celsius; unless otherwise indicated, all parts and percentages are by weight.

EXAMPLE 1

4-nitrophenylhydrazone of 4,4'-diaminobenzophenone [I]

To a stirred mixture of 4,4'-diaminobenzophenone (10.6 g. 50 mmol) (obtained from Ash-Stevens Co. Detroit, MI) and 4-nitrophenylhydrazine (8.42 g. 50 mmol allowing for 10% water in the commercial sample) in absolute ethanol (70 ml) were stirred and concentrated sulfuric acid (10 ml) was added dropwise and the mixture was stirred and refluxed for 2 hr. and 20 min. After the mixture was set aside overnight, the yellow precipitate was isolated by filtration, washed with ethanol and ether and then transferred to a 1:1 beaker containing 400 ml of water. This suspension was stirred and potassium carbonate (40 g) was added slowly. After stirring for 1 hr. the orange-yellow solid was separated by filtration, washed with water, and dried to yield 15.4 g of the title compound (88.5% yield) mp 196°-198° C.; PMR (DMSO-$d_6$) $\delta$9.58 (s. 1H, NH), 8.05 (d, 2H, J=8.3 Hz, hydrogens ortho to nitro group), 7.28 (d, 2H, J=8.3 Hz, hydrogens meta to nitro group), 7.23 (d, 2H, J=8.4 Hz, hydrogens meta to the amino group, trans to the hydrazone), 6.95 (d, 2H, J=8.4 Hz, hydrogens meta to the amino group, cis to the hydrazone), 6.71 (d, 2H, J=8.4 Hz, hydrogens ortho to the amino group, trans to the hydrazone), 6.54 (d,2H, J=8.4 Hz hydrogens ortho to the amino group, cis to the hydrazone), 5.47 (s, 2H, amino group hydrogens trans to the hydrazone), and 5.42 (s, 2H, amino group hydrogens cis to the hydrazone).

EXAMPLE 2

4-nitrophenylhydrazone of 3,3'-diaminobenzophenone [II]

A mixture of 3,3'-diaminobenzophenone (obtained from Ash-Stevens Co.) (15.4 g, 0.0725 mol), ethanol (100 ml), 4-nitrophenylhydrazine (12.3 g, 0.0725 mol allowing for 10% water present in the commercial sample), and acetic acid (5 ml) was stirred and heated under reflux for 21 hr. After cooling to room temperature the yellow precipitate was filtered off, washed with 20 ml of ethanol and then with 50 ml of hexane. The title compound was obtained as yellow micro-crystals, mp 202°-205° C., 23.9 g, 91% yield. PMR (DMSO-$d_6$) $\delta$9.63 (s, 1H, hydrazone NH), 8.09 (d, 2H, J=8.4 Hz, Ho), 7.36 (d, 2H, J=8.4 Hz, Hm), 7.22-6.40 (m, 8H, aromatic), 5.30 (s, 2H, NH$_2$), and 5.11 (s, 2H, NH$_2$).

EXAMPLE 3

2,4-dinitrophenylhydrazone of 4,4'-diaminobenzophenone [III]

The title compound was obtained as brown, amorphous powder, mp 270°-273° C. (dec.), in 91.9% yield by following the procedure reported for compound (I) using 4,4'-diaminobenzophenone and 2,4-dinitrophenylhydrazine.

EXAMPLE 4

2,4-dinitrophenylhydrazone of 3,4-diaminobenzophenone [IV]

The above derivative was prepared the same way as (I); amorphous brown powder, ca. 1:2 mixture of geometric isomers; mp 295°-297° C. (dec.); 87% yield.

EXAMPLE 5

N'-methyl-N'-(3-hydroxy-4-nitrophenyl)hydrazone of m-aminoacetophenone [V]

A mixture of m-aminoacetophenone (4.5 g. 33 mmol), 50 ml of ethanol, N'-methyl-N'-(3-hydroxy-4-nitrophenyl)hydrazine (5.5 g. 30 mmol), and 5 ml of acetic acid was heated under reflux for 36 hr. After cooling, the precipitate was filtered and recrystallized from ethanol to provide the title compound as yellow-orange crystals, mp 124°–126° C. (5.9 g 65.5% yield). PMR spectrum in DMSO-$d_6$ was consistent with the structure.

EXAMPLE 6

4-aminobenzoylhydrazone of 3-hydroxy-4-nitrobenzaldehyde [VI]

The title compound was obtained by refluxing a mixture of 60 mmol each of 4-aminobenzhydrazide and 3-hydroxy-4-nitrobenzaldehyde (both from Aldrich) in 300 ml of ethanol and 50 ml of acetic acid for 2 hr. Product was obtained as yellow, amorphous solid, mp 275°–277° C., 17.4 g. 95% yield. PMR spectrum was in agreement with structure.

EXAMPLE 7

4-Nitrophenylhydrazone of 3-aminoacetophenone [VII]

A mixture of 3-aminoacetophenone (13.5 g, 0.1 mol), 4-nitrophenylhydrazine (16.9 g, 0.1 mol allowing for 10% water) and 150 ml ethanol was stirred and 12 ml acetic acid was added. The mixture was heated under reflux for 2 hr. and filtered while hot to remove small amounts of dark solid. The filtrate was concentrated to ~70 ml, cooled, and the dark yellow solid was filtered. Recrystallization from ethanol gave the title compound as yellow-brown crystals (13.5 g, 50% yield), mp 176°–78° C. The $^1$H NMR spectrum (DMSO-$d_6$) indicated that the product obtained was 1:1 mixture of cis- and trans-isomers.

EXAMPLE 8

4-Nitrophenylhydrazone of 4-aminoacetophenone [VIII]

The title compound was obtained as orange-yellow, amorphous powder, mp 218°–220° C., in 90% yield, by following the procedure described for example 7.

EXAMPLE 9

4-Tricyanovinylphenylhydrazone of 4,4'-diaminobenzophenone (IX)

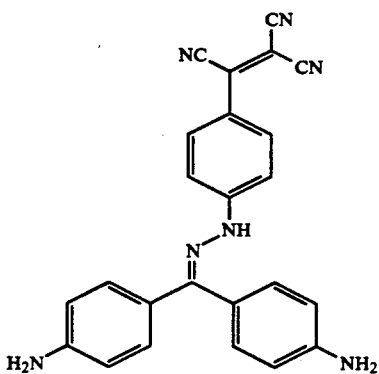

To a stirred mixture of 4,4'-diaminobenzophenone (2.5 g. 12 mmol), 1-formyl-2-(4-tricyanovinylphenyl)hydrazine (2.5 g, 10.6 mmol) and 65 ml of ethanol was added a mixture of water (5 ml) and conc. sulfuric acid (10 ml). The mixture was heated and stirred under reflux for 1 hr, cooled, and the purple precipitate was filtered and washed with 2×20 ml of ethanol. The solid was suspended in 150 ml of water and 40 ml of a saturated aq. solution of sodium bicarbonate was added with good agitation. After stirring for 15 min., the green-black crystalline solid was collected, washed with water to provide 4 g of the title hydrazone (94% yield) mp 260°–262° C.; $^1$H NMR (DMSO-$d_6$) δ10.4 (br s, 1H, NH), 7.80 (d, 2H, J=7.0 Hz), 7.25 (m, 4H), 6.93 (d, 2H, J=7.0 Hz), 6.67 (d, 2H, J=7.8 Hz), 6.53 (d, 2H, J=7.3 Hz), 5.56 (s, 2H, 4-amino), and 5.51 (s, 2H, 4'-amino).

EXAMPLE 10

6-Nitro-2-benzothiazolylhydrazone of 4,4'-diaminobenzophenone (X)

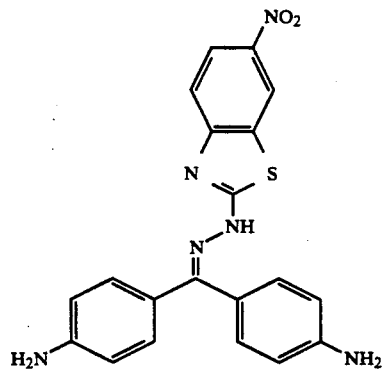

A mixture of 6-nitro-2-benzothiazolylhydrazine (3.18 g 15 mmol), 4,4'-diaminobenzophenone (3.2 g, 15 mmol), ethanol (60 ml) and 3 ml of conc. sulfuric acid was stirred and heated under reflux for 4 hr. After stirring for another 2 hr at room temperature, the yellow precipitate was filtered, washed with 2×20 ml of ethanol and then suspended in 1 liter of water. Addition of 350 ml of a saturated aq. solution of sodium bicarbonate led to the precipitation of a dark yellow precipitate which was filtered and washed with water. The title compound was obtained as deep yellow, amorphous powder and weighed 5.5 g (90% yield) mp 268°–270° C.; $^1$H NMR (DMSO-$d_6$) δ11.8 (br s, 1H, NH), 8.70 (br s, 1H), 8.12 (dd. 1H, $J_1$=8.9 Hz, $J_2$=2.5 Hz), 7.36 (d, 1H, J=8.9 Hz), 7.24 (d, 2H, J=8.6 Hz), 6.96 (d, 2H, J=8.6 Hz), 6.64 (d, 2H, J=8.6 Hz), 6.54 (d, 2H, J=8.6 Hz), 5.56 (br s, 2H, NH$_2$), and 5.47 (br s, 2H, NH$_2$').

Measurement of the NLO Activity of the Amino Aryl Hydrazones

The second-order NLO activities of the amino aryl hydrazone of Examples 1, 2, 3, 5 and 9 were determined in solution using the Electric Field Induced Second Harmonic Generation (EFISH) technique (see B. F. Levine and C. G. Bethea, J. Chem. Phys., 63, 2666, 1975). A pulsed voltage of 5 KV was applied to electrodes in a solution cell with 2 mm electrode separation. The 5 KV pulses were synchronized with the firing of the laser (25 Hz). The input and output windows were sandwiched between the electrodes to achieve a wedge angle of approximately 3.08° across the cell. The second harmonic generation (SHG) signal created by the solution was detected with a photomultiplier and was measured over a range of solution concentrations and normalized to the signal from a quartz reference wedge. The $\mu\beta$ product for the test molecule was determined from the SHG data as described by Levine and Bethea, supra. The excitation wavelength used was with 1064 nm from a QuantaRay DCR-2a Nd$^{3+}$/Yag laser, or 1579 nm by Raman shifting (in H$_2$ gas at 400 psi) the 532 nm frequency doubled (using a KDP crystal) output of the same laser. The results for the measurements of $\mu\beta$, conducted at 1064 nm fundamental excitation, are shown in Table I. Some of these values are approaching the highest $\mu\beta$ values reported to date. Also shown are the solvents that were used.

TABLE I

| Compound | $\mu\beta/10^{-48}$ esu | $\epsilon 532/M^{-1}cm^{-1}$ | $\lambda_{abs, max}$/nm |
| --- | --- | --- | --- |
| I (THF) | −1950 | 159 | 431 |
| II (THF) | −680 | 8.0 | 406 |
| III (DMF) | −152[b] | 3390 | 439 |
| V (THF) | −600 | 32 | 424 |
| IX (DMF) | −2469[b] | — | 580 |

[b]conducted at 1579 nm

EXAMPLE 11

I/DADS/TGE/DGE [XI]

To a mixture of triglycidylether of 4,4',4"-trihydroxyphenyl methane (4.40 g, 0.028 eq), (TGE) commercially available as Tactix ® 742 from The Dow Chemical Company; and diglycidylether of bisphenol A (1.10 g, 0.0061 eq), (DGE) commercially available as D.E.R. ® 383 from The Dow Chemical Company; was added a mixture of 4,4'-diaminodiphenyl sulfone (1.53 g, 0.025 eq), DADS; and I (0.75 g, 0.0086 eq). The DGE was used as a diluent at 25% w/w to decrease the viscosity of the mixture. The flask was evacuated and backfilled with N$_2$ several times as the flask was gradually heated to ~100° C. The mixture was then slowly heated up to 150° C. for ~10 min. The mixture became more viscous and the flask was cooled to room temperature by submerging the flask in a water bath. The resulting solid product was soluble in common organic solvents such as tetrahydrofuran (THF), diglyme, and dimethylacetamide.

EXAMPLE 12

II/DADS/TGE/DGE [XII]

This prepolymer was prepared in the manner described above. To a mixture of TGE (4.83 g, 0.030 eq) and DGE (1.22 g, 0.0068 eq) was added a mixture of DADS (1.15 g, 0.019 eq) and II (164 g, 0.019 eq). The DGE was used as a diluent at 25% w/w to decrease the viscosity of the mixture. The flask was evacuated and backfilled with N$_2$ several times as the flask was gradually heated up to ~100° C. The mixture was then heated at 150° C. for ~5 mins. The resulting solid product was soluble in common organic solvents as described above.

EXAMPLE 13

II/TGE/DGE [XIII]

This prepolymer was prepared in the manner described above for I/DADS/TGE/DGE except that II (3.24 g, 0.0037 eq, or 3.7 meq), TGE (4.52 g, 0.028 eq), and DGE (1.51 g, 0.0087 eq), were heated at 145° C. for ~5 min.

Prepolymers XIV (I/TGE/DGE), XV (II/DGE/DADS), and XVI (IV/TGE/DGE) were prepared in the manner as described in the examples above.

EXAMPLE 14

I/CEN/[XVII]

To a mixture of a cresol epoxy novolac resin (10.38 g, 0.052 eq), (CEN) represented by the formula:

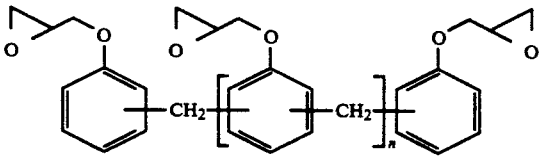

and I (4.52 g, 0.052 eq) was added freshly distilled THF (70 mls). The solvent was allowed to evaporate in air for ~48 hours. The resulting mixture was placed in a vacuum oven. The temperature was maintained at ~50° C. under ~30" Hg vacuum for 8 hours. The resulting solid product was soluble in common organic solvents as describe above.

EXAMPLE 15

Poly(amino ether) from Bisphenol A Diglycidyl Ether and VII [XVIII]

A 100 ml mini reactor equipped with mechanical stirrer, N$_2$ inlet, and thermometer, was charged with bisphenol A diglycidyl ether (6.664 g, 19.1 mmol, 1.01 equiv) and VII (5.105 g, 18.9 mmol). 1-phenoxy-2-propanol (DOWANOL TM PPh glycol ether) (18 mL) was added under a stream of nitrogen. The mixture was heated to 170° C. for 30 min., at which time A-1 catalyst (10 drops) was added. A-1 catalyst is ethyl triphenyl phosphonium acetate, 70% in methanol/acetic acid. The temperature of the mixture was increased to 175° C., and heating was continued for 2 h. The mixture was allowed to cool to room temperature overnight. Heating was resumed at 175° C. for an additional 1.5 h., at which time the viscosity began to increase noticeably. The mixture was allowed to cool, and additional DOWANOL TM PPh (15 mL) was added. DMF (50 mL) was added to the mixture, which was then poured into a water; methanol mixture (1:1, 500 mL) in a Waring blender. The precipitant was decanted, and the product was washed with a mixture of water and methanol (3:1, 500 mL) in the blender jar for 20 min. The product was collected by suction filtration and was air dried. The product was dissolved in THF (100 mL) and was reprecipitated into water as described above. The product was collected by filtration and was dried in a vacuum oven at 65° C. overnight. Obtained 10.66 g product (91% yield). The product had an inherent viscosity in DMF of 0.51 dL/g at 25° C., and a T$_g$ of 90° C. The $^1$H NMR spectrum was consistent with the proposed structure.

EXAMPLE 16

Poly(amino ether) from Bisphenol A Diglycidyl Ether and VIII [XIX]

Poly(amino ether) XIX was prepared in the same manner as poly(amino ether) XVIII with a reaction time of 3.25 h. The product was isolated by precipitation into a water:methanol mixture (3:1, 500 mL) as described above. The product had an inherent viscosity of 0.24 dL/g in DMF at 25° C., and a $T_g$ of 94° C. The $^1$H NMR spectrum was consistent with the proposed structure.

Preparation of a Film of the Polymer

Thin films (~1.5 μm) were prepared by either spin coating or dip coating. Spin coating was performed in a clean room using a Solitec Model 5100 spin coater. Dip coating was accomplished in a laminar flow hood by inserting the substrate into a rectangular jar containing ~10 mL solution and tipping the jar sideways to wet the substrate with the solution. The jar was then slowly brought to a vertical position and the solvent was allowed to evaporate with the jar cover on. Typically, THF was used as the solvent for dip coating and dimethylacetamide (DMAc) was used for spin coating. DMAc was selected as the solvent for spin coating because it produced the highest quality films. Polymer concentration ranged from 20–30% w/w depending on the viscosity of the solution.

The case films were air dried for at least 24 h. followed by extensive vacuum oven drying. The drying schedule was very important for these materials because solvent must be removed from the film at a temperature low enough such that further reaction or crosslinking will not occur. For epoxy polymers in which DADS was the curing agent, films could be dried at 130° C. without causing significant reaction. For I and II, the maximum drying temperature was 80° C. due to the higher reactivity of these amine curing agents. Amounts of residual solvent in films was not determined after drying, but residual solvent could be detected by the presence of relatively high currents during the parallel plate poling process.

The samples were poled using either corona poling (CP) or parallel plate (PP) poling techniques. The NLO activity coefficient $d_{33}$ was determined at 1064 nm or 1579 nm fundamental excitation by second harmonic generation measurements relative to a quartz crystal using the Maker Fringe rotation method (see K. D. Singer, et al. Appl. Phy. Lett., 49 248, 1986).

Table II shows the compositions prepared and results for $T_g$, and $d_{33}$ for the compositions.

TABLE II

| Monomer[a] | Tg (°C.) | $d_{33}{}^c$ ($10^{-9}$ esu) at 532 nm | Poling Type |
|---|---|---|---|
| I/DADS/TGE/DGE (XI) | >250 | 4.4 | cp |
| II/DADS/TGE/DGE (XII) | >250 | 11<br>8.6 | cp<br>pp |
| II/TGE/DGE(XIII) | 235 | 18 | pp |
| I/TGE/DGE(XIV) | >250 | 58 | pp |
| II/DGE/DADS (XV) | 235 | 15 | cp |
| IV/TGE/DGE (XVI) | >250 | 5.4 | cp |
| I/CEN (XVII) | >230 | 14[d] | pp |
| VII/DGE(XVIII) | 90 | 24 | cp |
| VIII/DGE (XIX) | 94 | 22 | cp |

[a]75/25 molar ratio of TGE/DGE unless indicated otherwise.
[c]measured at 532 nm at 0.5M V/cm.
[d]measured at 790 nm at 1.0M V/cm.

Thermal Stability

The thermal stability of the poled films of the thermoset polymeric compositions XIII and XVII were evaluated by measuring the NLO activity coefficient $d_{33}$ following 100° C. exposure in a recirculating air oven. The results are shown in Table III.

TABLE III

| Polymers | Days at 100° C. | $d_{33}$ ($10^{-9}$ esu) |
|---|---|---|
| XIII[c] | 0 | 18 |
| | 51 | 16 |
| | 71 | 9 |
| | 174 | 6 |
| | 264 | 4 |
| XVII[d] | 0 | 14 |
| | 18 | 13 |
| | 39 | 12 |
| | 46 | 12 |

[c]measured at 532 nm at 0.5M V/cm
[d]measured at 790 nm at 1.0M V/cm

It has been found that the thermoset polymeric composition XVI maintains about 52% of its original activity after aging for about 60 days at 200° C. in a vacuum oven, clearly showing that dipolar orientation stability can be maintained for short excursions at elevated temperatures, which may be required for some processing steps.

What is claimed is:

1. A nonlinear optical polymeric composition comprising the reaction product of:
   (A) at least one compound containing an average of more than one epoxy group per molecule; and
   (B) at least a first reactant, the first reactant being an aminoaryl hydrazone, represented by the formula:

wherein Ar is an aromatic carbocyclic or heterocyclic radical containing up to 30 non-hydrogen atoms, optionally substituted with a functionality capable of reacting with an epoxy group; A is independently at each occurrence either R or an aromatic group, optionally substituted with a functionality capable of reacting with an epoxy group; D is nil, carbonyl or sulfonyl; and R is hydrogen or a $C_1$ to $C_{20}$ hydrocarbyl radical; provided there is at least one aromatically substituted electron withdrawing group, and at least two active aromatic amino hydrogens capable of reacting with an epoxy group, in the aminoaryl hydrazone.

2. The nonlinear optical polymeric composition of claim 1, wherein Ar is selected from the group consisting of:

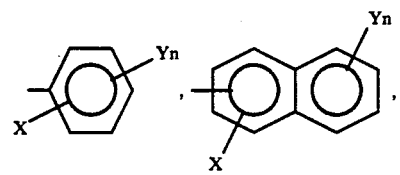

-continued

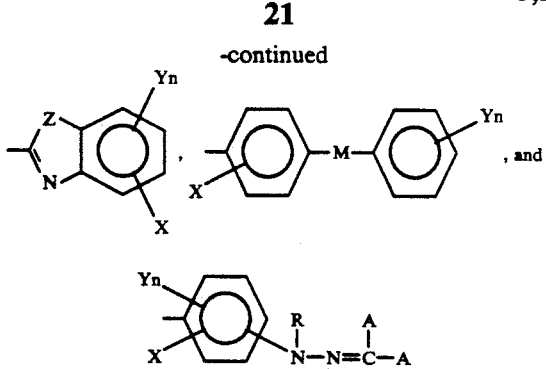

wherein X is hydrogen or a functionality capable of reacting with an epoxy group; Z is selected from the group consisting of O, S, and NR; M is either a covalent bond or a divalent conjugated group; Y is a hydrogen or an electron-withdrawing group; n is an integer from 1 to 5, and R is as defined hereinabove, provided that when X is a hydrogen, Y is not a hydrogen and wherein A is as hereinbefore defined.

3. The nonlinear optical polymeric composition of claim 2, wherein the divalent conjugated group is selected from the group consisting of —C≡C—, —CR=CR—, —CR=CR—CR=CR—, —CR=N—, —N=CR—, and —N=N—, wherein R is as defined hereinabove.

4. The nonlinear optical polymeric composition of claim 2, wherein Y is selected from the group consisting of —$NO_2$, —$SO_2R$, —$SO_2CH_2F$, —$SO_2CHF_2$, —$SO_2CF_3$, —$S(NSO_2CF_3)CF_3$, —$CF_3$, —$CO_2R$, —$COCF_3$, cyano, cyanovinyl, dicyanovinyl, and tricyanovinyl, wherein R is a hydrogen or a $C_1$ to $C_{20}$ hydrocarbyl group.

5. The nonlinear optical polymeric composition of claim 2, wherein the functionality capable of reacting with the epoxy group is selected from group consisting of —OH, —$NH_2$, —NHR, —$CO_2H$, —SH, —CHO, CONHR, —COCl, —COOCOR, —Cl, and —OOH; wherein R is hydrogen, or a $C_1$ to $C_{20}$ hydrocarbyl radical.

6. The nonlinear optical polymeric composition of claim 2, wherein component (A) is an epoxy compound containing an average of more than one glycidyl group per molecule.

7. The nonlinear optical polymeric composition of claim 2, wherein the epoxy compound is selected from the group consisting of glycidyl ethers, glycidyl esters, and glycidyl amines.

8. The nonlinear optical composition of claim 7, wherein A at each occurrence is independently

wherein X and Y are as defined hereinabove, and m+n is equal to 5, provided that when X is a hydrogen, Y is not a hydrogen.

9. The nonlinear optical composition of claims 2 or 8, wherein the first reactant contains a primary aromatic amino group as a first functionality capable of reacting with the epoxy group.

10. The nonlinear optical composition of claim 9, wherein the first reactant further contains at least a second functionality capable of reacting with the epoxy group.

11. The nonlinear optical composition of claims 2 or 8, wherein the component (B) further contains a second reactant.

12. The nonlinear optical composition of claims 2 or 8, wherein the component (A) further contains a second epoxy-containing compound.

13. The nonlinear optical composition of claim 10, wherein the second functionality capable of reacting with the epoxy group is an aromatic primary amino or an aromatic hydroxyl group.

14. The nonlinear optical composition of claim 13, wherein R is hydrogen, Ar is 4-nitrophenyl, D is a covalent bond, and A at each occurrence is 4-aminophenyl.

15. The nonlinear optical composition of claim 13, wherein R is hydrogen, Ar is 2,4-dinitrophenyl, D is a covalent bond, and A at each occurrence is 4-aminophenyl.

16. The nonlinear optical composition of claim 13, wherein R is H, Ar is 4-nitrophenyl, D is a covalent bond, and A at each occurrence is 3-aminophenyl.

17. The nonlinear optical composition of claim 13, wherein R is H, Ar is 2,4-dinitrophenyl, D is a covalent bond, and A at each occurrence is phenyl, and 3,4-diaminophenyl, respectively.

18. The nonlinear optical composition of claim 13, wherein R is methyl, Ar is 3-hydroxy-4-nitrophenyl, D is a covalent bond, and A at each occurrence is methyl and 3-aminophenyl, respectively.

19. The nonlinear optical composition of claim 13, wherein R is hydrogen, Ar is 4-aminophenyl, D is a carbonyl, R is hydrogen and A at each occurrence is hydrogen and 3-hydroxy-4-nitrophenyl, respectively.

20. The nonlinear optical composition of claim 9, wherein R is hydrogen, Ar is 4-nitrophenyl, D is a covalent bond, and A at each occurrence is methyl and 3-aminophenyl, respectively.

21. The nonlinear optical composition of claim 9, wherein R is hydrogen, Ar is 4-nitrophenyl, D is a covalent bond, and A at each occurrence is methyl, and 4-aminophenyl, respectively.

22. The nonlinear optical polymeric composition of claim 14, wherein the component (A) is a mixture of diglycidyl ether of bisphenol A, and triglycidyl ether of 4,4',4''-trihydroxyphenyl methane.

23. The nonlinear optical polymeric composition of claim 17, wherein the component (A) is a mixture of diglycidyl ether of bisphenol A and triglycidylether of 4,4',4''-trihydroxyphenyl methane.

24. The nonlinear optical polymeric composition of claim 16, wherein the component (A) is a mixture of diglycidyl ether of bisphenol A, and triglycidyl ether of 4,4',4''-trihydroxyphenyl methane.

25. The nonlinear optical polymeric composition of claim 20, wherein the component (A) is a diglycidyl ether of bisphenol A.

26. The nonlinear optical polymeric composition of claim 21, wherein the component (A) is a diglycidyl ether of bisphenol A.

27. The nonlinear optical polymeric composition of claim 22, wherein the component (B) further comprises a second reactant.

28. The nonlinear optical polymeric composition of claim 27, wherein the second reactant is 4,4'-diaminophenyl sulfone.

29. The nonlinear optical polymeric composition of claim 24, wherein the component (B) further comprises a second reactant.

30. The nonlinear optical polymeric composition of claim 29, wherein the second reactant is 4,4'-diaminophenyl sulfone.

31. The nonlinear optical polymeric composition of claim 14, wherein component (A) is represented by the formula:

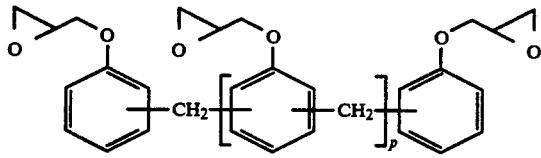

wherein p is from 0.1 to 10.

32. The nonlinear optical polymeric composition of claim 16, wherein component (A) is diglycidyl ether of bisphenol A and component (B) further comprises a second reactant.

33. The nonlinear optical polymeric composition of claim 32, wherein the second reactant is 4,4'-diaminophenyl sulfone.

34. An article comprising the nonlinear optical polymeric composition of claim 1.

35. A process for preparing a nonlinear optical composition of claim 1, comprising applying an electric field to the composition.

36. A process for preparing a nonlinear optical composition of claim 1, comprising substantially simultaneously
 (i) polymerizing a mixture of the component (A) and the component (B); and
 (ii) applying an electric field to the mixture to form a material having nonlinear optical properties.

* * * * *